US011844556B2

(12) United States Patent
DelMonaco et al.

(10) Patent No.: US 11,844,556 B2
(45) Date of Patent: Dec. 19, 2023

(54) SURGICAL REDUCTION TOOLS AND METHODS FOR ACHIEVING BONE COMPRESSION

(71) Applicant: ARTHREX, INC., Naples, FL (US)

(72) Inventors: Alex DelMonaco, Chelmsford, MA (US); Cory Schultz, Naples, FL (US); Paul Fein, Maynard, MA (US)

(73) Assignee: ARTHREX, INC., Naples, FL (US)

( * ) Notice: Subject to any disclaimer, the term of this patent is extended or adjusted under 35 U.S.C. 154(b) by 57 days.

(21) Appl. No.: 17/544,098

(22) Filed: Dec. 7, 2021

(65) Prior Publication Data

US 2023/0172646 A1 Jun. 8, 2023

(51) Int. Cl.
*A61B 17/80* (2006.01)
*A61B 17/17* (2006.01)
*A61B 17/68* (2006.01)
*A61B 17/84* (2006.01)

(52) U.S. Cl.
CPC .......... *A61B 17/8019* (2013.01); *A61B 17/17* (2013.01); *A61B 17/808* (2013.01); *A61B 17/8014* (2013.01); *A61B 17/842* (2013.01); *A61B 17/848* (2013.01); *A61B 2017/681* (2013.01)

(58) Field of Classification Search
CPC .............. A61B 17/17; A61B 2017/681; A61B 17/8019; A61B 17/808; A61B 17/848; A61B 17/8897
See application file for complete search history.

(56) References Cited

U.S. PATENT DOCUMENTS

| | | | | |
|---|---|---|---|---|
| 3,534,731 | A * | 10/1970 | Jean-Nicolas | A61B 17/8004 606/105 |
| 4,388,921 | A * | 6/1983 | Sutter | A61B 17/8047 411/537 |
| 7,704,257 | B2 * | 4/2010 | Murner | A61B 17/8019 606/86 R |
| 8,721,693 | B2 * | 5/2014 | Cawley | A61B 17/8605 606/289 |
| 8,778,000 | B2 * | 7/2014 | Haddad | A61B 17/1728 606/290 |
| 9,119,645 | B2 * | 9/2015 | McBride | A61B 17/1757 |

\* cited by examiner

*Primary Examiner* — Larry E Waggle, Jr.
(74) *Attorney, Agent, or Firm* — Carlson, Gaskey & Olds, P.C.

(57) ABSTRACT

Surgical reduction tool assemblies may be used for achieving compression between bone fragments or across joints when performing arthrodesis procedures, bone fracture procedures, etc. The reduction tool assemblies may be used to reduce a gap between bone fragments or between bones of a joint prior to attempting to achieve final compression with a bone plate.

20 Claims, 10 Drawing Sheets

SURGICAL REDUCTION TOOLS AND METHODS FOR ACHIEVING BONE COMPRESSION

BACKGROUND

This disclosure relates to the field of surgery, and more particularly to surgical reduction tool assemblies and associated surgical methods for achieving bone-to-bone compression during surgical procedures.

Bone plates are commonly employed during orthopedic surgeries to stabilize, fuse, and/or align bones or bone fragments in order to restore functionality to a joint. A gap between bones/bone fragments typically must be reduced to achieve bony apposition prior to attempting to accomplish final compression with the bone plate.

SUMMARY

This disclosure is directed to reduction tool assemblies and associated surgical methods for achieving bony apposition during surgical procedures (e.g., bone fusion procedures), bone fracture procedures, osteotomy procedures, etc.

An exemplary reduction tool assembly for use during surgical procedures may include, inter alia, a sleeve and an insert. The insert is receivable within the sleeve and includes an off-center through hole. The insert is rotatable relative to the sleeve to move the off-center through hole along an arced path between a first position and a second position.

An exemplary surgical system may include, inter alia, a bone plate, a reduction tool assembly configured to engage an opening of the bone plate, and a K-wire. The reduction tool assembly includes a sleeve and an insert rotatably received within the sleeve. The K-wire is received through the insert. The insert is rotatable relative to the sleeve to move the K-wire along an arced path between a first position and a second position.

An exemplary surgical method may include, inter alia, securing a bone plate to a first bone with a first K-wire, securing a reduction tool assembly to the bone plate at a location above a second bone, inserting a second K-wire through an insert of the reduction tool assembly and into the second bone, rotating the insert from a first position to a second position relative to a sleeve of the reduction tool assembly. The rotating moves the second K-wire along an arced path, thereby nudging the second bone toward the first bone.

DETAILED DESCRIPTION

This disclosure is directed to reduction tool assemblies for achieving compression between bone fragments or across joints when performing arthrodesis procedures, bone fracture procedures, etc. The reduction tool assemblies of this disclosure may be used to reduce a gap between bone fragments or between bones of a joint prior to attempting to achieve final compression with a bone plate. These and other features of this disclosure are described in further detail below.

An exemplary reduction tool assembly for use during surgical procedures may include a sleeve and an insert. The insert is receivable within the sleeve and includes an off-center through hole. The insert is rotatable relative to the sleeve to move the off-center through hole along an arced path between a first position and a second position In a further embodiment, a first position of an insert of a reduction tool assembly is an externally biased position and a second position is an internally biased position relative to a sleeve of the assembly.

In a further embodiment, a sleeve and an insert of a reduction tool assembly are coaxial along a longitudinal centerline axis when the insert is accommodated within an internal bore of the sleeve.

In a further embodiment, an off-center through hole of an insert is offset from a longitudinal centerline axis of a reduction tool assembly.

In a further embodiment, an off-center through hole of an insert of a reduction tool assembly includes a star pattern adapted for receiving a driver.

In a further embodiment, an off-center through hole of an insert of a reduction tool assembly includes an alignment marking adapted for visually indicating whether the off-center through hole is positioned in the first position or the second position relative to a sleeve of the assembly.

In a further embodiment, a sleeve of a reduction tool assembly includes an internal bore including a groove.

In a further embodiment, a radial spring is accommodated within a groove of a sleeve of a reduction tool assembly. The radial spring is configured to apply a radial force against an insert of the assembly.

In a further embodiment, a sleeve of a reduction tool assembly includes an internal bore having a stepped configuration.

In a further embodiment, a piston of an insert of a reduction tool assembly is accommodated within an internal bore of a sleeve of the assembly.

An exemplary surgical system may include a bone plate, a reduction tool assembly configured to engage an opening of the bone plate, and a K-wire. The reduction tool assembly includes a sleeve and an insert rotatably received within the sleeve. The K-wire is received through the insert. The insert is rotatable relative to the sleeve to move the K-wire along an arced path between a first position and a second position.

In a further embodiment, a first position of an insert of a reduction tool assembly is an externally biased position and a second position is an internally biased position relative to a bone plate of the system.

In a further embodiment, a K-wire of a surgical system is received through an off-center through hole of an insert of a reduction tool assembly.

In a further embodiment, an off-center through hole of an insert of a reduction tool assembly is offset relative to a longitudinal centerline axis of the reduction tool assembly.

In a further embodiment, a sleeve of a reduction tool assembly includes a tip portion having a thread that is adapted to engage an opening of a bone plate.

An exemplary surgical method may include securing a bone plate to a first bone with a first K-wire, securing a reduction tool assembly to the bone plate at a location above a second bone, inserting a second K-wire through an insert of the reduction tool assembly and into the second bone, rotating the insert from a first position to a second position relative to a sleeve of the reduction tool assembly. The rotating moves the second K-wire along an arced path, thereby nudging the second bone toward the first bone.

In a further embodiment, a gap between a first bone and a second bone is reduced as a K-wire of a surgical system is moved along an arced path.

In a further embodiment, a first position of an insert of a reduction tool assembly is an externally biased position and a second position is an internally biased position relative to a bone plate.

In a further embodiment, an insert of a reduction tool assembly includes an alignment marking for visually indicating a first position and a second position of the insert.

In a further embodiment, a K-wire is received through a second insert of a second reduction tool. The second insert is rotated from a first position to a second position relative to a second sleeve of the second reduction tool assembly. The K-wire is moved along a second arced path that nudges a first bone toward a second bone.

Figure 1:
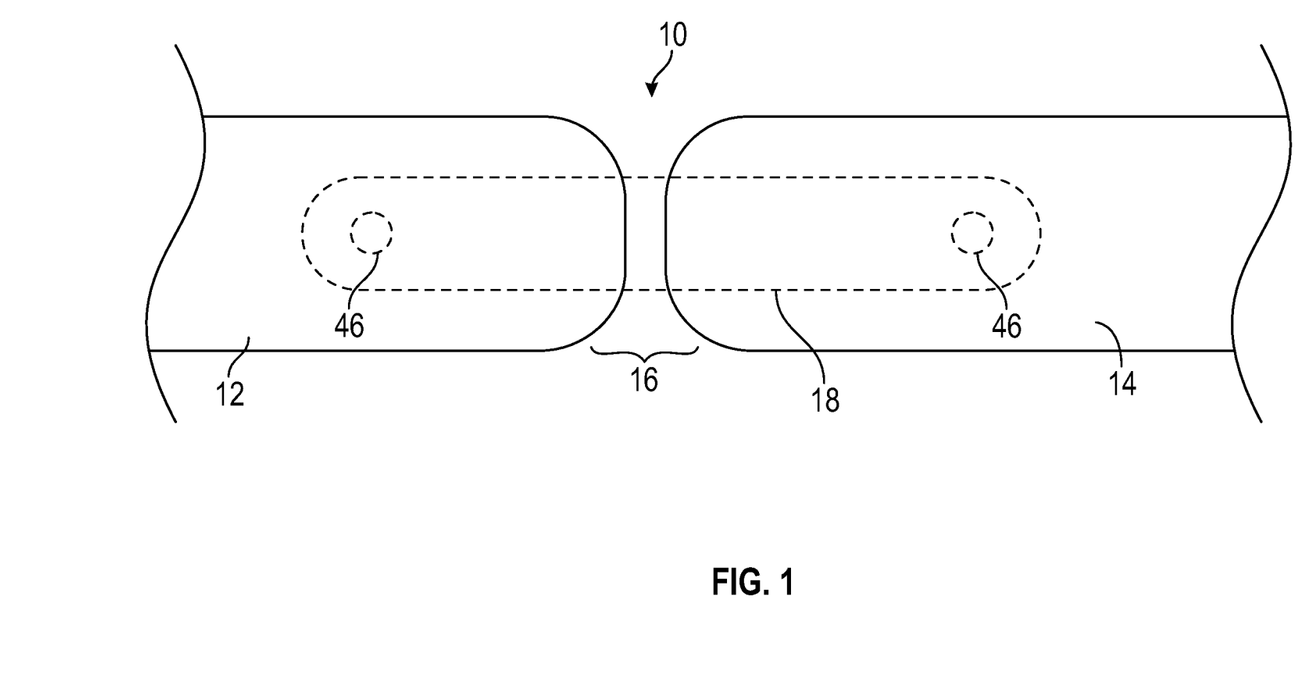
FIG. 1 illustrates select portions of a human musculoskeletal system.

FIG. 1 schematically illustrates select portions of a joint 10 of the human musculoskeletal system. The joint 10 could be any joint of the musculoskeletal system of the human body. In an embodiment, the joint 10 is a joint of a foot, such as the metatarsophalangeal (MTP) joint, for example. However, the teachings of this disclosure are not limited to the foot and could equally apply to the ankle, hand, wrist, etc.

The joint 10 may include a first bone 12 and a second bone 14. The first bone 12 and the second bone 14 may be different bones or segments of the same bone. When a sports injury or accident occurs, the first bone 12 and the second bone 14 may become separated from one another. The separated pieces of bone typically must be reapproximated to one another prior to being fused together to facilitate proper healing and stability.

A bone plate 18 is commonly used to perform arthrodesis or fusion procedures in order to fuse the first bone 12 and the second bone 14 together for restoring functionality to the joint 10. The bone plate 18 is shown schematically using broken lines in FIG. 1 because its specific design is not intended to limit this disclosure.

A gap 16 may extend between the first bone 12 and the second bone 14. The gap 16 may be larger than is appropriate as a result of the injury/accident and thus may need to be reduced prior to fusing the first and second bones 12, 14 together with the bone plate 18. If not properly reduced, the gap 16 can lead to malunion and potential revision surgeries. This disclosure is therefore directed to reduction tools and associated surgical methods for optimally preparing the joint 10 by reducing the gap 16 and maintaining the reduction to a final bony apposition prior to implantation of the bone plate 18 or some other compression device.

Figure 2:
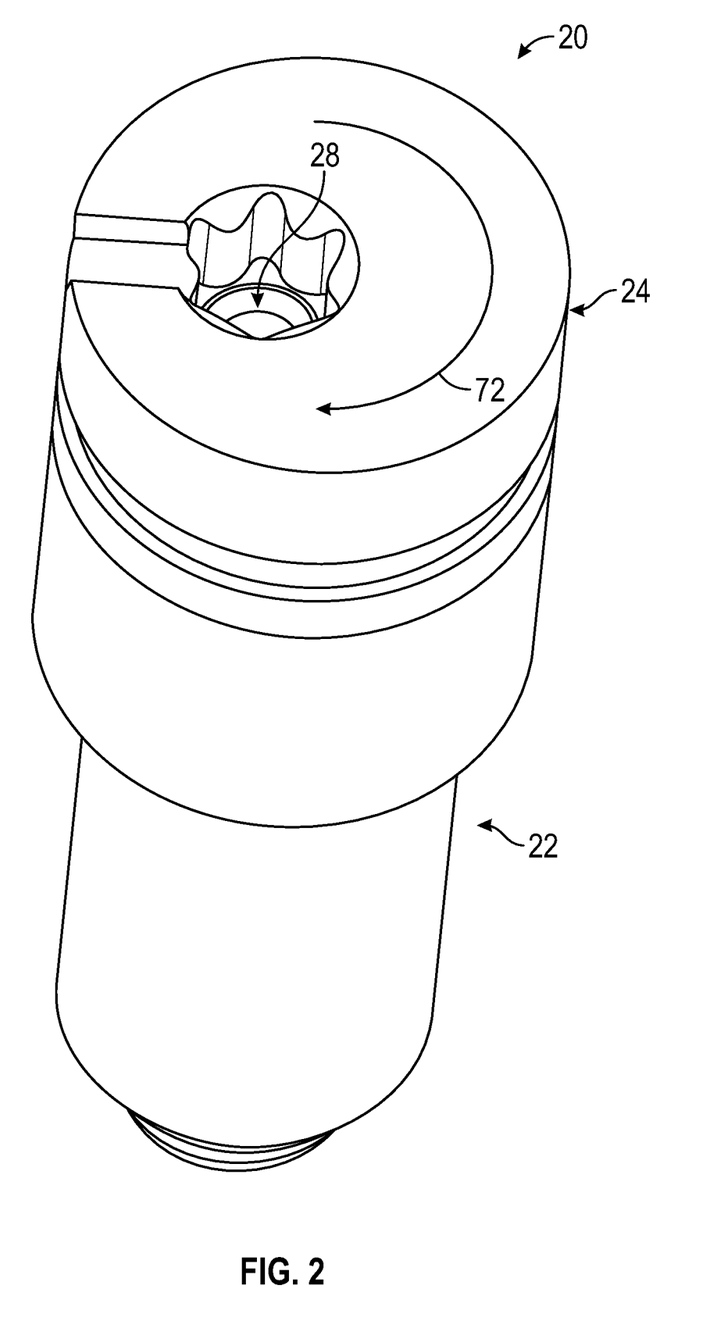
FIG. 2 is a perspective view of an exemplary reduction tool assembly for achieving compression during a surgical procedure.
Figure 3:
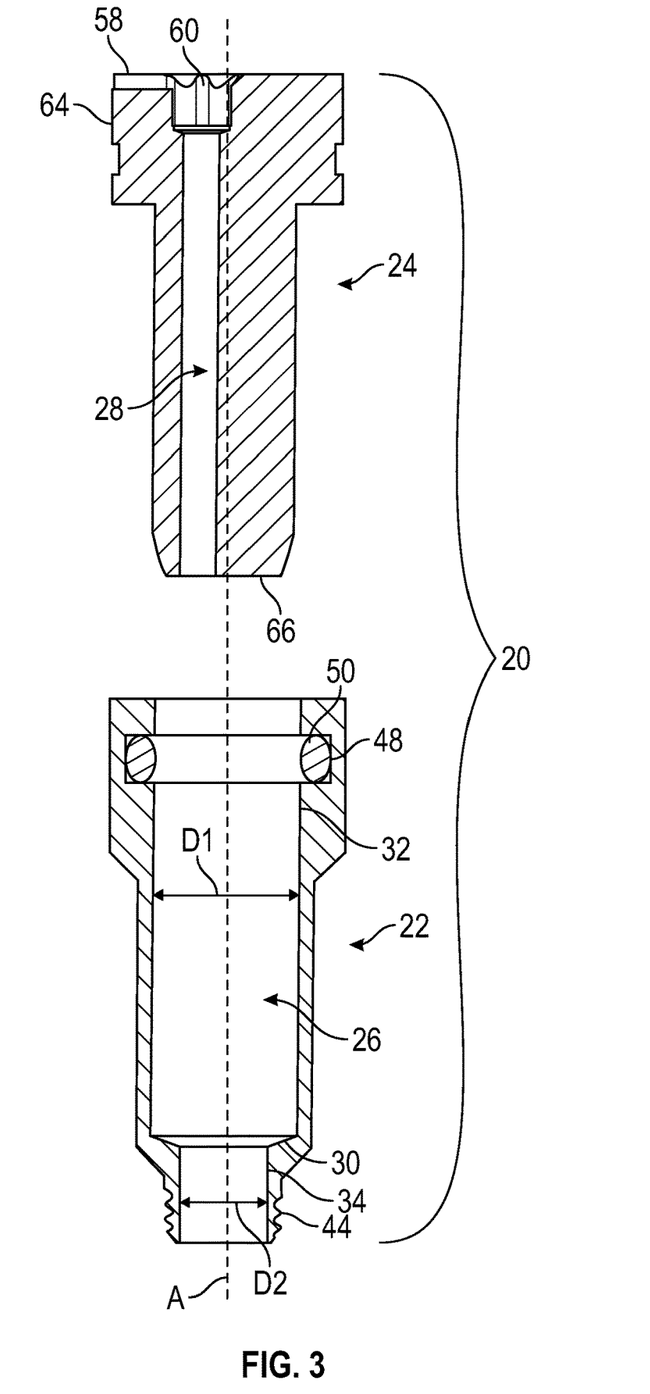
FIG. 3 is a cross-sectional exploded view of the reduction tool assembly of FIG. 2.

FIGS. 2 and 3, with continued reference to FIG. 1, illustrate an exemplary reduction tool assembly 20. The reduction tool assembly 20 could also be referred to as a reduction tower assembly. The reduction tool assembly 20 may be used to reduce the gap 16 and achieve and maintain bony apposition between the first and second bones 12, 14 prior to attempting to achieve final compression with the bone plate 18, for example.

The reduction tool assembly 20 may include a sleeve 22 and an insert 24 that may be positioned within the sleeve 22. When assembled, the insert 24 is received within an internal bore 26 (best shown in FIG. 3) of the sleeve 22. In an embodiment, the insert 24 is rotatable relative to the sleeve 22 once accommodated within the internal bore 26.

The reduction tool assembly 20 may extend along a longitudinal centerline axis A. The sleeve 22 and the insert 24 may be coaxial along the longitudinal centerline axis A when the insert 24 is accommodated within the sleeve 22.

The insert 24 of the reduction tool assembly 20 may include a through hole 28. The through hole 28 may be sized and shaped to accommodate another surgical instrument, such as a K-wire (not shown in FIGS. 2 and 3), for example. The through hole 28 may extend over an entire length of the insert 24. In an embodiment, the through hole 28 is offset from the longitudinal centerline axis A. The through hole 28 is therefore considered to be an "off-center" opening or passage that is formed through the insert 24.

The internal bore 26 of the sleeve 22 may include a narrowed region 30 (best shown in FIG. 3). The narrowed region 30 establishes a stepped/tapering configuration in which the diameter of the internal bore 26 reduces inside the sleeve 22. For example, the internal bore 26 may include a first section 32 having a first diameter D1 and a second section 34 having a second diameter D2 that is smaller than the first diameter D1 at a location inside the sleeve 22. The first section 32 may be proximal to the narrowed region 30, and the second section 34 may be distal to the narrowed region 30.

At least a portion of the insert 24 may be accommodated within the second section 34 of the internal bore 26 but without protruding beyond a distal tip of the sleeve 22 when the insert 24 is received within the sleeve 22. Thus, when surgical instrumentation such as a K-wire is accommodated within the through hole 28 of the insert 24, the instrumentation may extend to a location outside of the sleeve 22, such as for penetrating bone, for example.

As the insert 24 is rotated relative to the sleeve 22, the through hole 28 may move along an arced path 72. The through hole 28 may engage a K-wire or other surgical instrument as it moves, thereby forcing the K-wire to also travel along the arced path 72.

In an embodiment, both the sleeve 22 and the insert 24 are constructed of stainless steel. However, the material composition of each of the subcomponents of the reduction tool assembly 20 is not intended to limit this disclosure.

Figure 4:
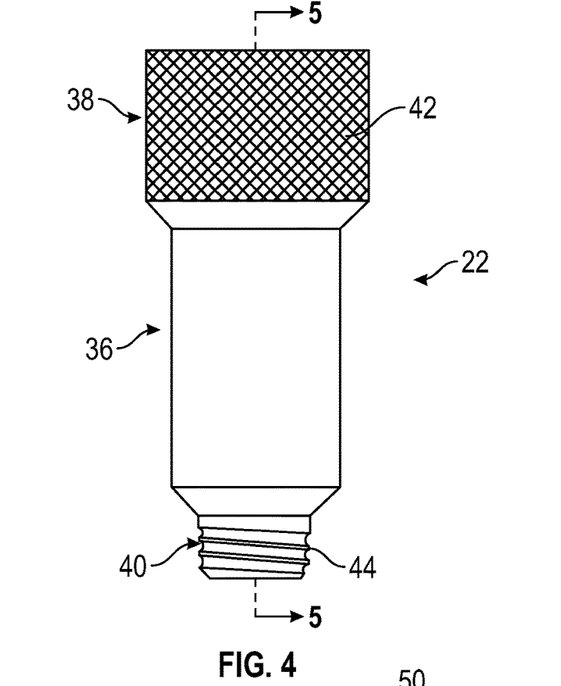
FIG. 4 is a front view of a sleeve of the reduction tool assembly of FIGS. 2-3.
Figure 5:
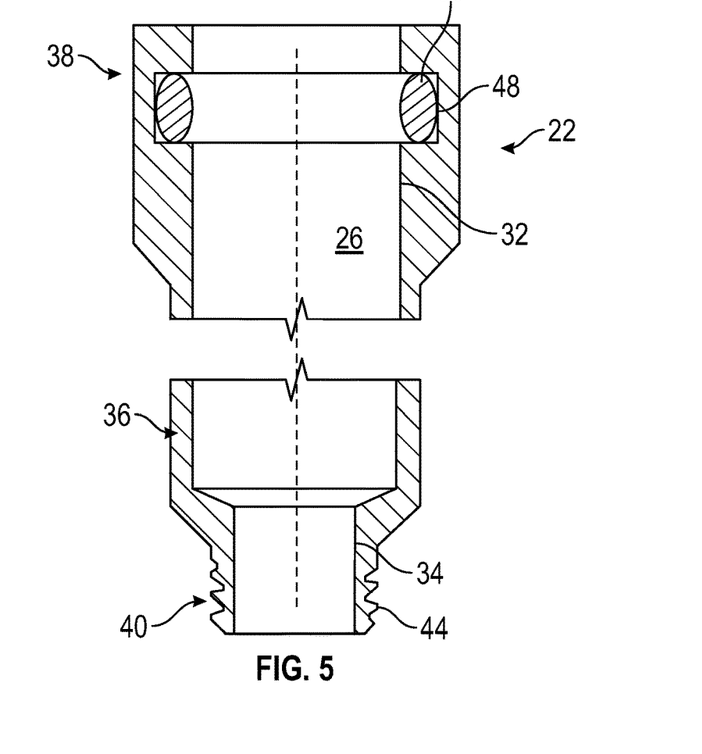
FIG. 5 is a cross-sectional view through section 5-5 of the sleeve of FIG. 4.

FIGS. 4 and 5, with continued reference to FIGS. 2-3, illustrate further details associated with the sleeve 22 of the reduction tool assembly 20. The sleeve 22 may include a shaft portion 36 that connects between a gripping portion 38, located proximally, and a tip portion 40, located distally.

The gripping portion 38 may include a knurled surface 42. The knurled surface 42 is designed to improve a user's grip when handling the sleeve 22.

The tip portion 40 may include a thread 44. The thread 44 may be circumferentially disposed about a radially outer surface of the tip portion 40. The thread 44 may be configured to engage a threaded opening 46 (see, e.g., FIG. 1) of the bone plate 18, for example.

The internal bore 26 of the sleeve 22 may include a groove 48 that extends radially outward from the first section 32 at a location inside the gripping portion 38 of the sleeve 22. The groove 48 may establish a shelf for accommodating a radial spring 50. The radial spring 50 is configured to apply a radial force on a portion (e.g., a piston) of the insert 24, thereby maintaining an axial positioning of the insert 24 relative to the sleeve 22. For example, the radial force applied by the radial spring 50 may prevent the insert 24 from sliding in a direction parallel to the longitudinal centerline axis A in the absence of a mechanical force of a sufficient magnitude being applied by the user.

FIGS. 6, 7, 8, and 9, with continued reference to FIGS. 2-3, illustrate further details associated with the insert 24 of the reduction tool assembly 20. The insert 24 may include a gripping portion 52, located proximally, and a piston 54 that extends distally away from the gripping portion 52. When the insert 24 is accommodated within the sleeve 22, the piston 54 is received within the internal bore 26, and the gripping portion 52 is located proximal to the gripping portion 38 of the sleeve 22 and is thus accessible outside of the internal bore 26.

The gripping portion 52 may include a knurled surface 56. The knurled surface 56 is designed to improve a user's grip when handling the insert 24, such as when rotating the insert 24 relative to the sleeve 22, for example.

Figure 6:
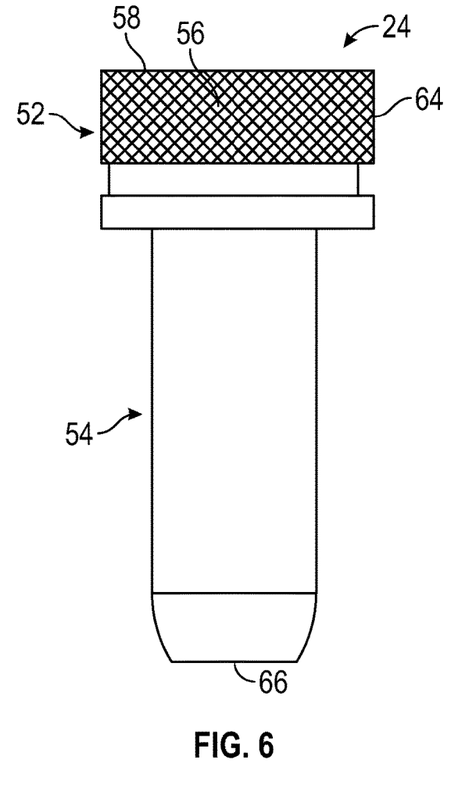
FIG. 6 is a front view of an insert of the reduction tool assembly of FIGS. 2-3.
Figure 7:
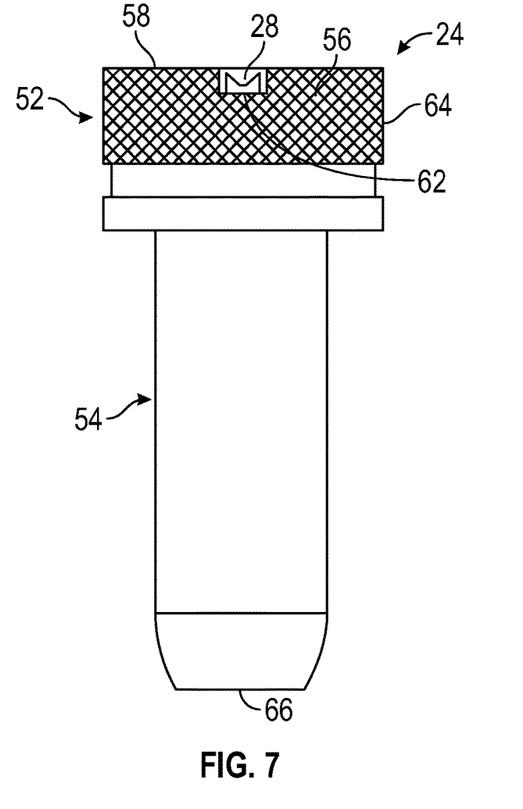
FIG. 7 is a side view of the insert of FIG. 6.
Figure 8:
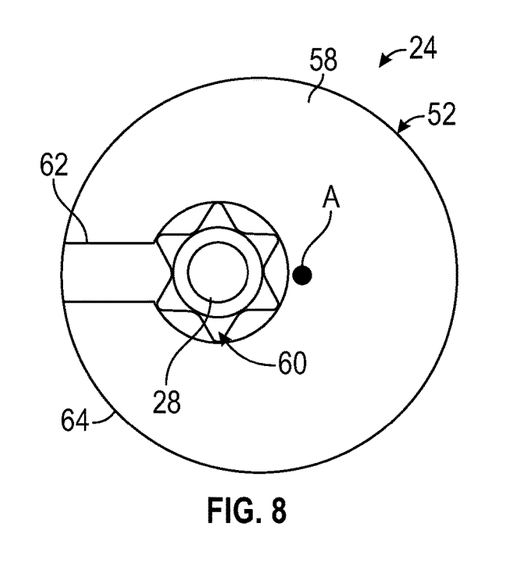
FIG. 8 is a top view of the insert of FIG. 6.

The through hole 28 may extend through both the gripping portion 52 and the piston 54 and is positioned at a location that is offset from the longitudinal centerline axis A. The through hole 28 may open through a top surface 58 of the gripping portion 52. A portion of the through hole 28 located near the top surface 58 may include a star pattern 60 (or any other pattern) for accommodating a driver (not shown) that can be used for rotating the insert 24 in the event rotation cannot be achieved by hand alone.

An alignment marking 62 may be provided on the top surface 58 of the gripping portion 52. The alignment marking 62 is designed to indicate to the user where the through hole 28 (and thus the K-wire) is in reference to the sleeve 22 (e.g., internally versus externally rotated) during surgical use to achieve bony apposition. The alignment marking 62 may take the form of a groove or an etching formed on the top surface 58. The alignment marking 62 may extend from the star pattern 60 of the through hole 28 to an outer circumferential surface 64 of the gripping portion 52.

Figure 9:
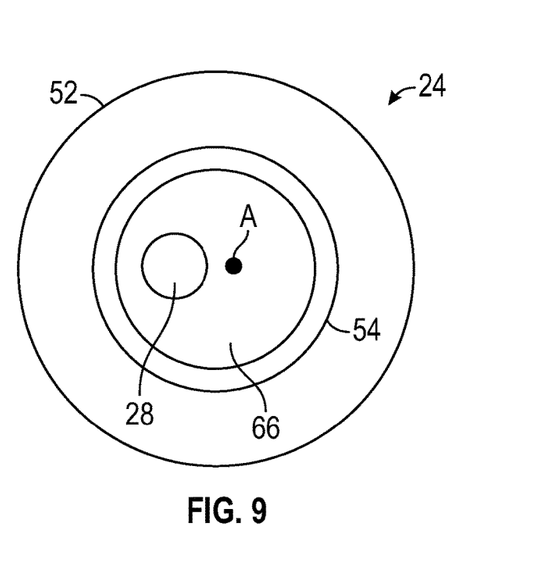
FIG. 9 is a bottom view of the insert of FIG. 6.

The through hole 28 may also open through a bottom surface 66 of the piston 54. Surgical instrumentation (e.g., a K-wire) may thus be passed completely through the insert 24 during surgical procedures.

FIGS. 10-14, with continued reference to FIGS. 1-9, schematically illustrate, in sequential order, an exemplary surgical method for creating compression across an arthrodesis site during an arthrodesis procedure, such as a MTP fusion, for example. Fewer or additional steps than are recited below could be performed within the scope of this disclosure. In addition, the recited order of steps depicted in FIGS. 10-14 is not intended to limit this disclosure.

Figure 10:
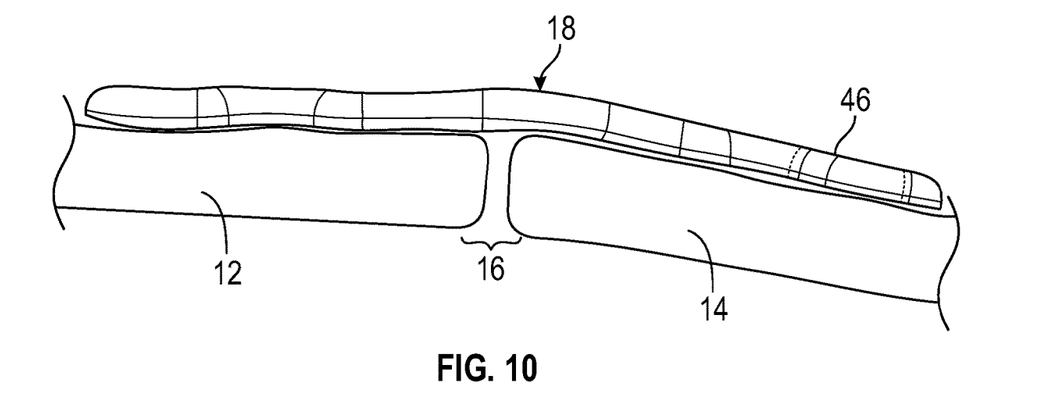
FIGS. 10, 11, 12, 13, and 14 schematically illustrate an exemplary surgical method for creating compression across an arthrodesis site according to an embodiment of this disclosure.

Referring first to FIG. 10, the bone plate 18 may be approximated to a desired position relative to the first bone 12 and the second bone 14. In this position, the bone plate 18 may span across the gap 16 between the first bone 12 and the second bone 14. The bone plate 18 may include any size, shape, and configuration so long as it includes at least one threaded opening 46 for accommodating the tip portion 40 of the sleeve 22 of the reduction tool assembly 20.

Figure 11:
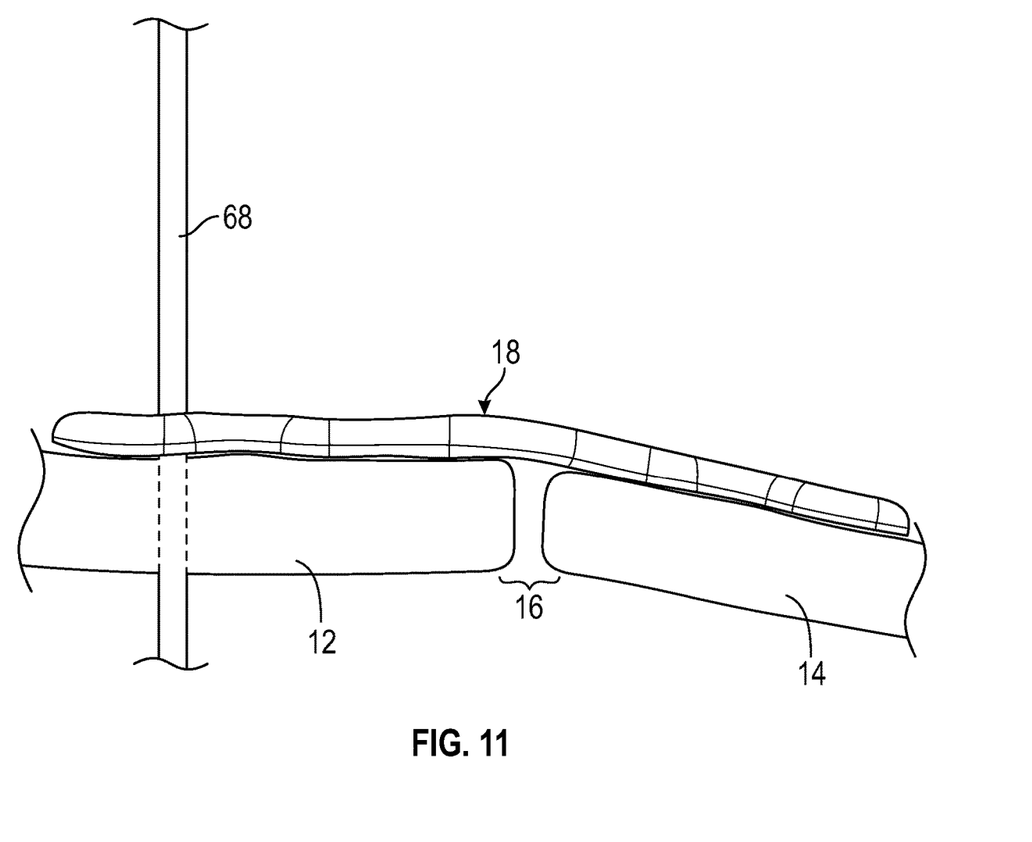

Next, as shown in FIG. 11, the bone plate 18 may be temporarily secured to the first bone 12 associated with the arthrodesis site. For example, a K-wire 68 may be inserted through the bone plate 18 and then into the underlying first bone 12 to temporarily fixate the bone plate 18 in place.

Figure 12:
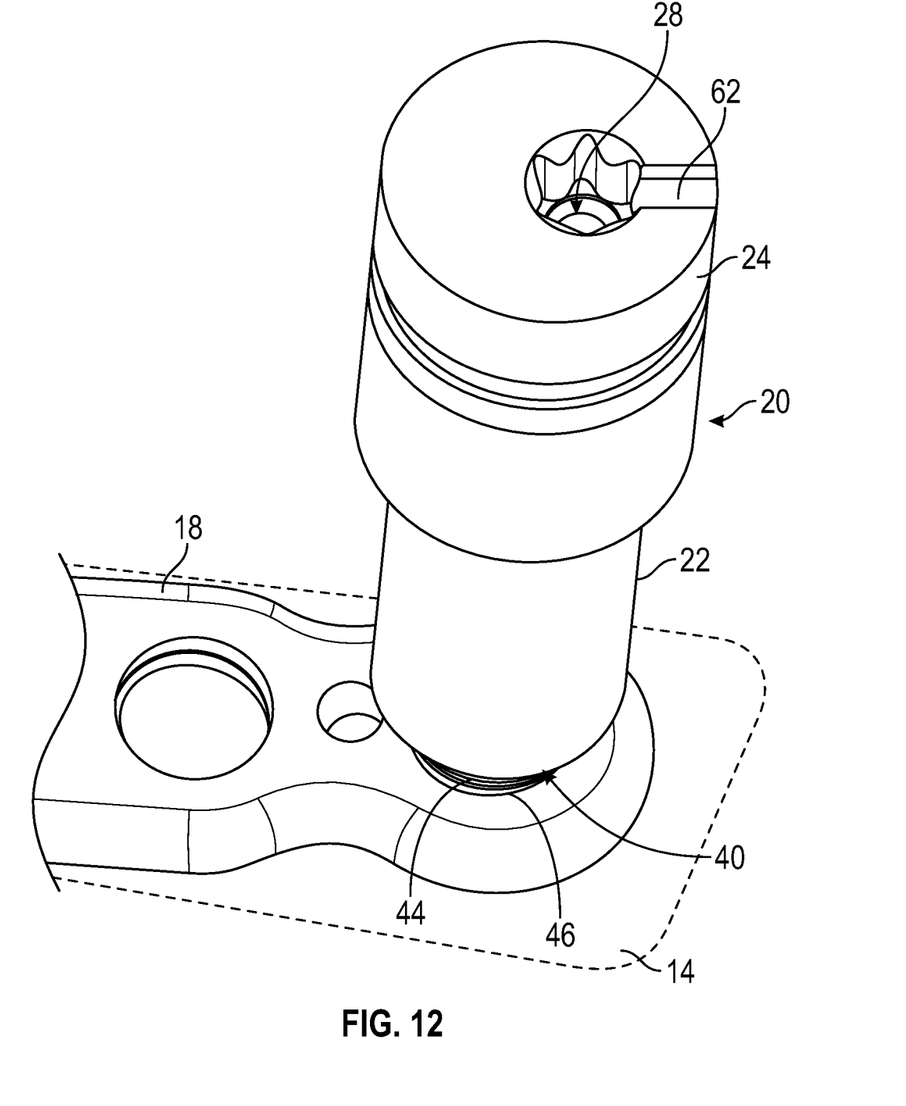
Figure 13:
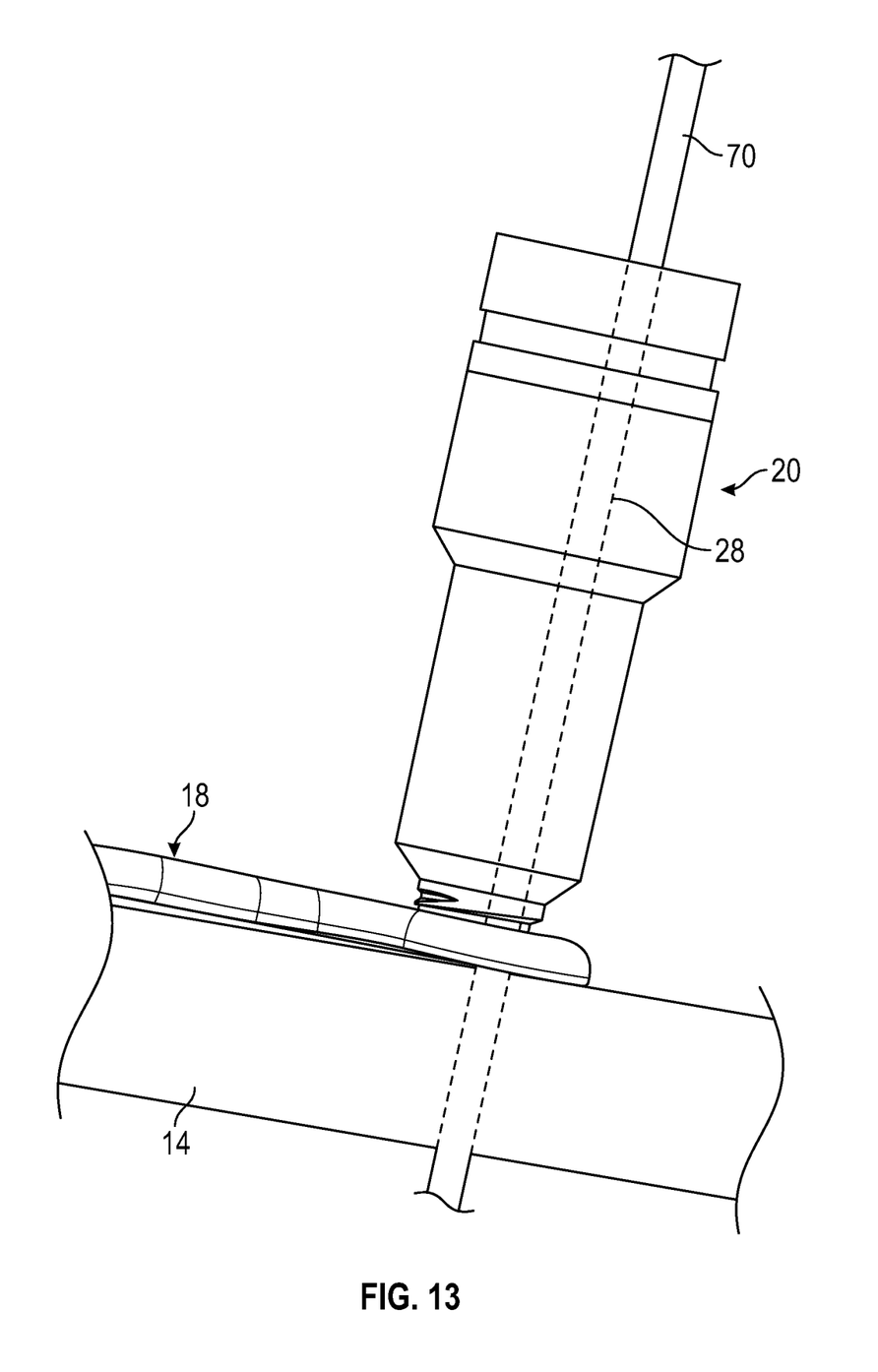

Referring now to FIG. 12, the pre-assembled reduction tool assembly 20 may then be secured to the threaded opening 46 of the bone plate 18. In this embodiment, the threaded opening 46 is positioned directly above the second bone 14. The reduction tool assembly 20 may be secured in place by screwing the tip portion 40 into the threaded opening 46, thereby allowing the thread 44 to engage the threaded opening 46. The reduction tool assembly 20 may be positioned such that the through hole 28 of the insert 24 (e.g., as indicted by the alignment marking 62) is biased externally (e.g., in a direction away from the first bone 12). A K-wire 70 may then be inserted through the through hole 28 and into the underlying second bone 14 (see FIG. 13).

Figure 14:
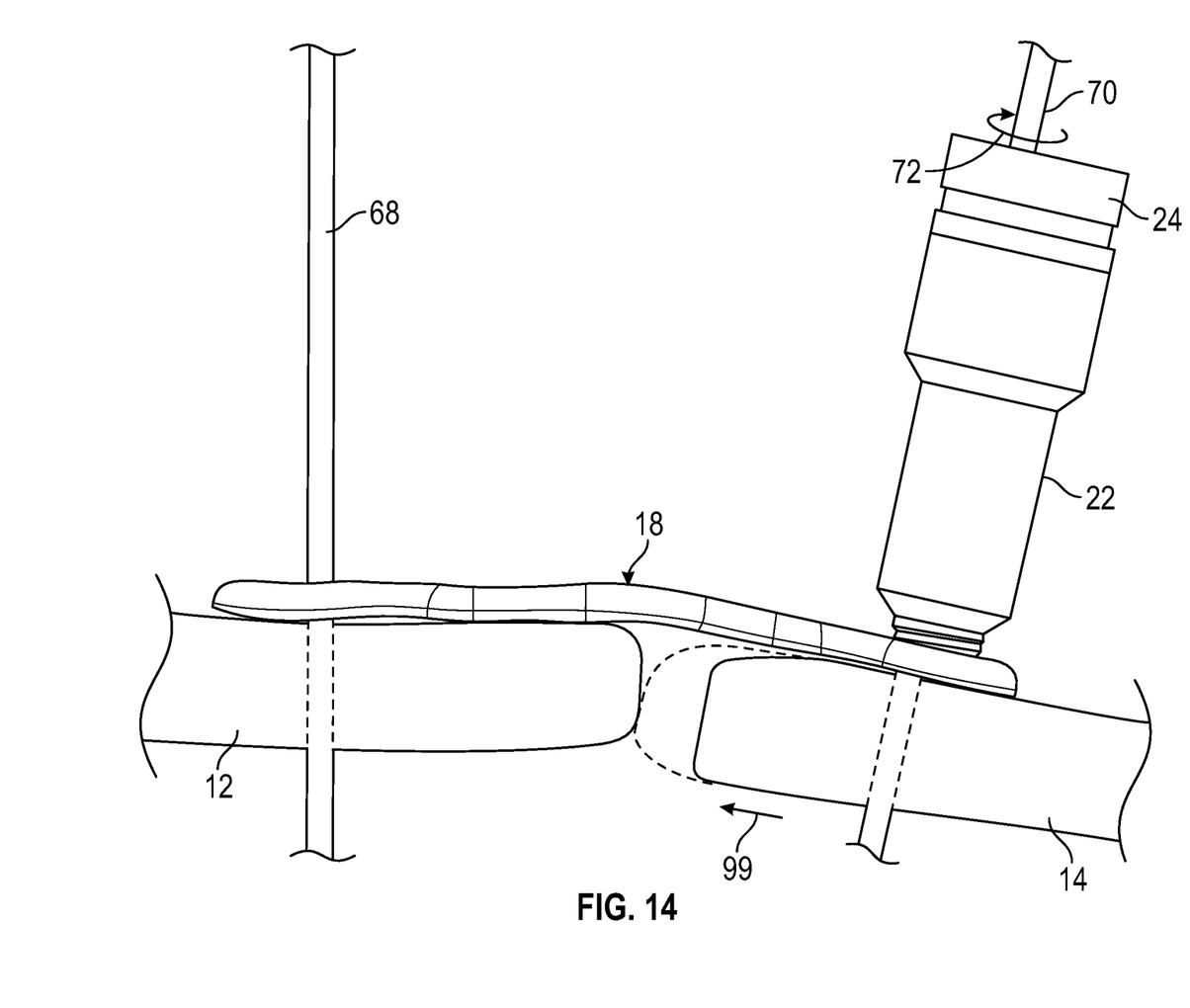

Next, as shown in FIG. 14, the insert 24 may be rotated relative to the sleeve 22. The insert 24 may therefore move from a first position (e.g., the externally biased position shown in FIG. 12) to a second position in which the through hole 28 is biased internally (e.g., in a direction toward the first bone 12). As the insert 24 is rotated, the through hole 28 may engage the K-wire 70, thereby causing the K-wire 70 to move along an arced path 72. Movement of the K-wire 70 along the arced path 72 nudges the second bone 14 toward the first bone 12 (schematically indicated by arrow 99), thus reducing the size of the gap 16 and creating compression across the arthrodesis site. Final compression may then be subsequently achieved by inserting one or more bone screws through the bone plate 18 and into each of the first bone 12 and the second bone 14.

Figure 15:
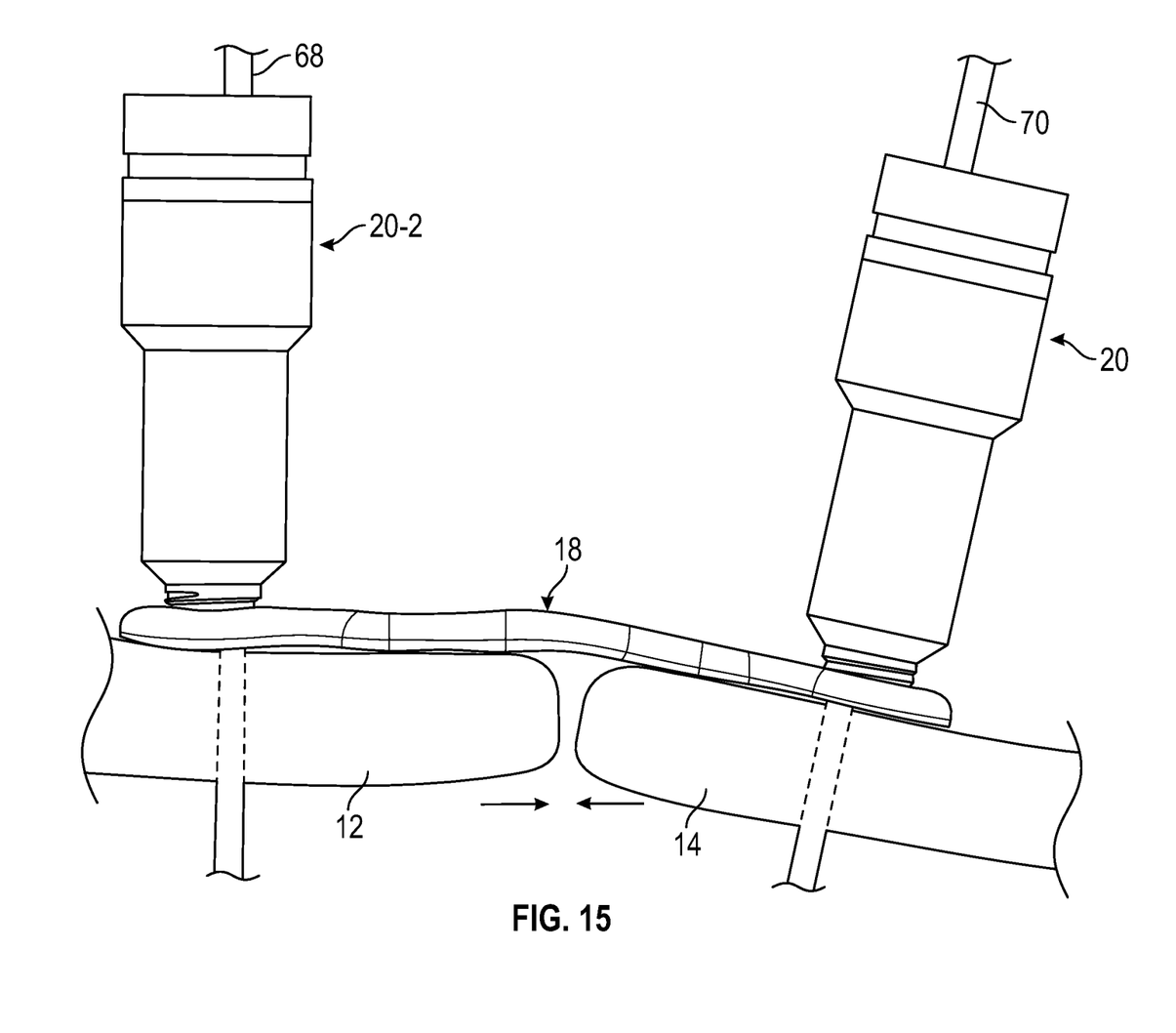
FIG. 15 illustrates the use of multiple reduction tool assemblies for achieving compression during a surgical procedure.

An additional reduction tool assembly 20-2 could be utilized in combination with the reduction tool assembly 20 and the bone plate 18 to double the possible reduction distance between the first and second bones 12, 14. In such an embodiment, the reduction tool assembly 20-2 could be utilized in combination with the K-wire 68. In still other embodiments, one reduction tool assembly 20 could be provided for each bone/bone fragment involved in the arthrodesis procedure and depending on the amount of compression that is ultimately desired/necessary for achieving bony apposition across the joint.

The reduction tool assembly 20 described above may be provided in combination with various other surgical instruments to construct a surgical system or surgical kit. Such a surgical system could include, for example, one or more reduction tool assemblies, one or more bone plates, one or more K-wires, etc. and may provide an innovative way to achieve bony apposition across a fusion or arthrodesis site.

The exemplary reduction tool assemblies of this disclosure may be utilized during the implantation of an orthopedic bone plate to achieve a fixed distance reduction between neighboring bones or bone fragments. The reduction tool assemblies described herein may be utilized with any bone plate equipped with a threaded opening, thereby providing a nearly universal compression device.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A reduction tool assembly for use during a surgical procedure, comprising:
    a sleeve that includes a threaded tip portion configured to engage a threaded opening; and
    an insert receivable within the sleeve and including an off-center through hole,
    wherein the insert is rotatable relative to the sleeve to move the off-center through hole along an arced path between a first position and a second position.

2. The reduction tool assembly as recited in claim 1, wherein the first position is an externally biased position and the second position is an internally biased position relative to the sleeve.

3. The reduction tool assembly as recited in claim 1, wherein the sleeve and the insert are coaxial along a longitudinal centerline axis when the insert is accommodated within an internal bore of the sleeve.

4. The reduction tool assembly as recited in claim 3, wherein the off-center through hole is offset from the longitudinal centerline axis.

5. The reduction tool assembly as recited in claim 1, wherein the off-center through hole includes a star pattern adapted for receiving a driver.

6. The reduction tool assembly as recited in claim 1, wherein the off-center through hole includes an alignment marking adapted for visually indicating whether the off-center through hole is positioned in the first position or the second position relative to the sleeve.

7. The reduction tool assembly as recited in claim 1, wherein the sleeve includes an internal bore including a groove, and further comprising a radial spring accommodated within the groove and configured to apply a radial force against the insert.

8. The reduction tool assembly as recited in claim 1, wherein the sleeve includes an internal bore having a stepped configuration.

9. The reduction tool assembly as recited in claim 8, wherein a piston of the insert is accommodated within the internal bore.

10. The reduction tool assembly as recited in claim 1, wherein the sleeve includes a shaft portion that extends between a gripping portion and the threaded tip portion, and further wherein an internal bore of the sleeve extends through each of the shaft portion, the gripping portion, and the threaded tip portion.

11. A surgical system, comprising:
    a bone plate;
    a reduction tool assembly configured to engage an opening of the bone plate,
    wherein the reduction tool assembly includes a sleeve and an insert rotatably received within the sleeve; and
    a K-wire received through the insert,
    wherein the insert is rotatable relative to the sleeve to move the K-wire along an arced path between a first position and a second position.

12. The surgical system as recited in claim 11, wherein the first position is an externally biased position and the second position is an internally biased position relative to the bone plate.

13. The surgical system as recited in claim 11, wherein the K-wire is received through an off-center through hole of the insert.

14. The surgical system as recited in claim 13, wherein the off-center through hole is offset relative to a longitudinal centerline axis of the reduction tool assembly.

15. The surgical system as recited in claim 11, wherein the sleeve includes a tip portion having a thread that is adapted to engage the opening of the bone plate.

16. A surgical method, comprising:
    securing a bone plate to a first bone with a first K-wire;
    securing a reduction tool assembly to the bone plate at a location above a second bone;
    inserting a second K-wire through an insert of the reduction tool assembly and into the second bone;
    rotating the insert from a first position to a second position relative to a sleeve of the reduction tool assembly,
    whereby the second K-wire is moved along an arced path that nudges the second bone toward the first bone.

17. The surgical method as recited in claim 16, wherein a gap between the first bone and the second bone is reduced as the second K-wire is moved along the arced path.

18. The surgical method as recited in claim 16, wherein the first position is an externally biased position and the second position is an internally biased position relative to the bone plate.

19. The surgical method as recited in claim 18, wherein the insert includes an alignment marking for visually indicating the first position and the second position.

20. The surgical method as recited in claim 16, wherein the first K-wire is received through a second insert of a second reduction tool, and the method further comprises:
    rotating the second insert from a first position to a second position relative to a second sleeve of the second reduction tool assembly,
    whereby the first K-wire is moved along a second arced path that nudges the first bone toward the second bone.

* * * * *

UNITED STATES PATENT AND TRADEMARK OFFICE
CERTIFICATE OF CORRECTION

| | | |
|---|---|---|
| PATENT NO. | : 11,844,556 B2 | Page 1 of 1 |
| APPLICATION NO. | : 17/544098 | |
| DATED | : December 19, 2023 | |
| INVENTOR(S) | : Alex DelMonaco, Cory Shultz and Paul Fein | |

It is certified that error appears in the above-identified patent and that said Letters Patent is hereby corrected as shown below:

On the Title Page

Item (72) Inventor Cory Schultz's information should read as follows:
--Cory Shultz, Naples, FL (US)--

Signed and Sealed this
Twelfth Day of November, 2024

Katherine Kelly Vidal
*Director of the United States Patent and Trademark Office*